United States Patent [19]

Imran

[11] Patent Number: 5,255,679
[45] Date of Patent: Oct. 26, 1993

[54] ENDOCARDIAL CATHETER FOR MAPPING AND/OR ABLATION WITH AN EXPANDABLE BASKET STRUCTURE HAVING MEANS FOR PROVIDING SELECTIVE REINFORCEMENT AND PRESSURE SENSING MECHANISM FOR USE THEREWITH, AND METHOD

[75] Inventor: Mir A. Imran, Palo Alto, Calif.

[73] Assignee: Cardiac Pathways Corporation, Sunnyvale, Calif.

[21] Appl. No.: 893,972

[22] Filed: Jun. 2, 1992

[51] Int. Cl.$^5$ .............................................. A61B 5/04
[52] U.S. Cl. ..................................... 128/642; 607/122
[58] Field of Search .................. 128/642, 783–786, 128/419 D; 604/105; 606/41, 45, 46

[56] References Cited

U.S. PATENT DOCUMENTS

| | | | |
|---|---|---|---|
| 4,660,571 | 5/1987 | Hess | 128/642 |
| 4,664,120 | 4/1987 | Hess et al. | 128/784 |
| 4,699,147 | 10/1987 | Chilson et al. | 128/642 |
| 4,807,626 | 2/1989 | McGirr | 128/328 |
| 4,940,064 | 7/1990 | Desai | 128/784 |
| 5,010,894 | 4/1991 | Edhag | 128/785 |

Primary Examiner—Stephen C. Pellegrino
Assistant Examiner—Mike Peffley
Attorney, Agent, or Firm—Flehr, Hohbach, Test, Albritton & Herbert

[57] ABSTRACT

An endocardial catheter for mapping and/or ablation for use in a chamber of a heart defined by a wall comprising a flexible elongate tubular member having proximal and distal extremities. A basket assembly is mounted on the distal extremity of the flexible elongate member. The basket assembly is movable between expanded and contracted positions. The basket assembly has electrodes carried thereby which are adapted to be moved into engagement with the wall of the heart. A push-pull element is provided having proximal and distal extremities extending longitudinally of the tubular member and extending beyond the distal extremity of the tubular member and movable axially of the tubular member. The basket assembly has proximal and distal extremities. The proximal extremity of the basket assembly is secured to the distal extremity of the tubular member. The distal extremity of the basket assembly is secured to the distal extremity of the push-pull element. The proximal extremity of the flexible elongate member is secured to the push-pull element for sensing the force being applied to the push-pull element by the basket assembly as the heart is beating to ascertain whether or not the electrodes carried by the basket assembly are in continuous engagement with the wall of the heart during beating of the heart.

13 Claims, 2 Drawing Sheets

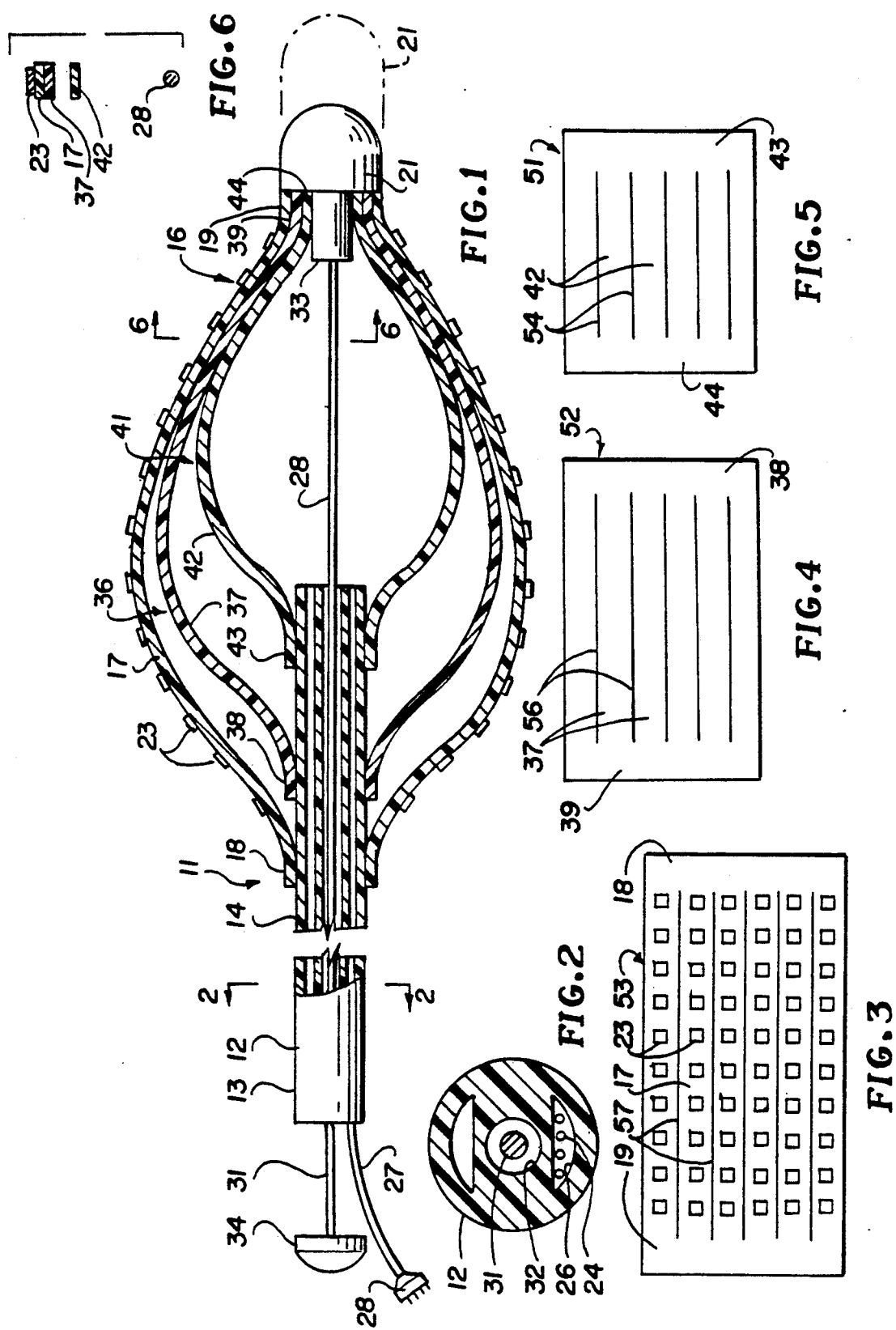

ENDOCARDIAL CATHETER FOR MAPPING AND/OR ABLATION WITH AN EXPANDABLE BASKET STRUCTURE HAVING MEANS FOR PROVIDING SELECTIVE REINFORCEMENT AND PRESSURE SENSING MECHANISM FOR USE THEREWITH, AND METHOD

This invention relates to an endocardial catheter for mapping and/or ablation with an expandable basket structure having means for providing selective reinforcement and pressure sensing mechanism for use therewith, and method.

In co-pending application Ser. No. 07/656,764 filed Feb. 15, 1991, entitled "ENDOCARDIAL MAPPING AND ABLATION SYSTEM AND CATHETER PROBE AND METHOD" now U.S. Pat. No. 5,156,151 there is disclosed a basket-like structure which can be expanded and contracted for movement into and out of engagement with the wall of a chamber of the heart, as for example the left ventricle. In certain applications, it has been found that the arms forming the basket-like structure are too flexible and the electrodes carried thereby do not always remain in engagement with the wall of the chamber during the pumping or beating of the heart. There is therefore a need for a new and improved endocardial catheter for napping and ablation which overcomes these deficiencies.

In general, it is an object of the present invention to provide an endocardial catheter for napping and/or ablation with a basket-type structure having means in the form of an inner expandable device for providing selective reinforcement for firmly but yieldably retaining the electrodes carried by the outer expandable device in contact with the moving wall of the beating heart.

Another object of the invention is to provide a catheter of the above character in which a plurality of inner expandable reinforcement devices are provided.

Another object of the invention is to provide a catheter of the above character in which the inner expandable devices are of different sizes.

Another object of the invention is to provide a catheter of the above character in which the inner expandable devices are of different lengths.

Another object of the invention is to provide a catheter of the above character in which the inner expandable devices are provided with arms which yieldably engage the arms of the outer expandable basket-like device to selectively reinforce the same.

Another object of the invention is to provide a catheter of the above character which is provided with a pressure sensing mechanism to ascertain when the expandable basket is in contact with the wall forming the chamber in the heart.

Additional objects and features of the invention will appear from the following description in which the preferred embodiments are set forth in detail in conjunction with the accompanying drawings.

FIG. 1 is a cross sectional view of the distal extremity of an endocardial catheter for mapping and/or ablation having means incorporating the present invention for providing selective reinforcement in the form of an inner expandable device.

FIG. 2 is a cross sectional view taken along the line 2—2 of FIG. 1.

FIG. 3 is a plan view of a flexible sheet utilized for making the primary, first or outer expandable basket-like device shown in FIG. 1.

FIG. 4 is a plan view of the flexible sheet used for making the secondary or second inner expandable basket-like device shown in FIG. 1.

FIG. 5 is a plan view of the flexible sheet utilized for making the tertiary or third expandable basket-like device shown in FIG. 1.

FIG. 6 is a cross sectional view taken along the line 6—6 of FIG. 1.

Figure 7:
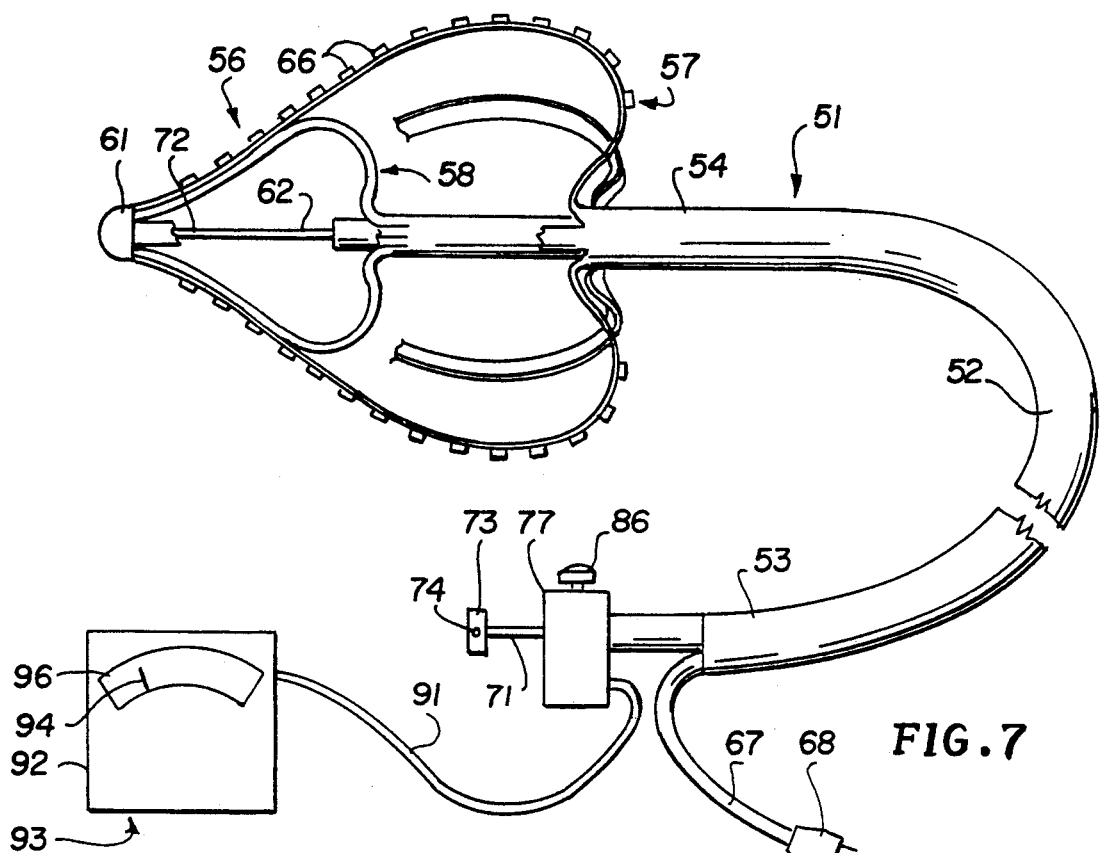
FIG. 7 is a side elevational view of an endocardial catheter of the above character with a pressure sensing mechanism for use therewith.
Figure 8:
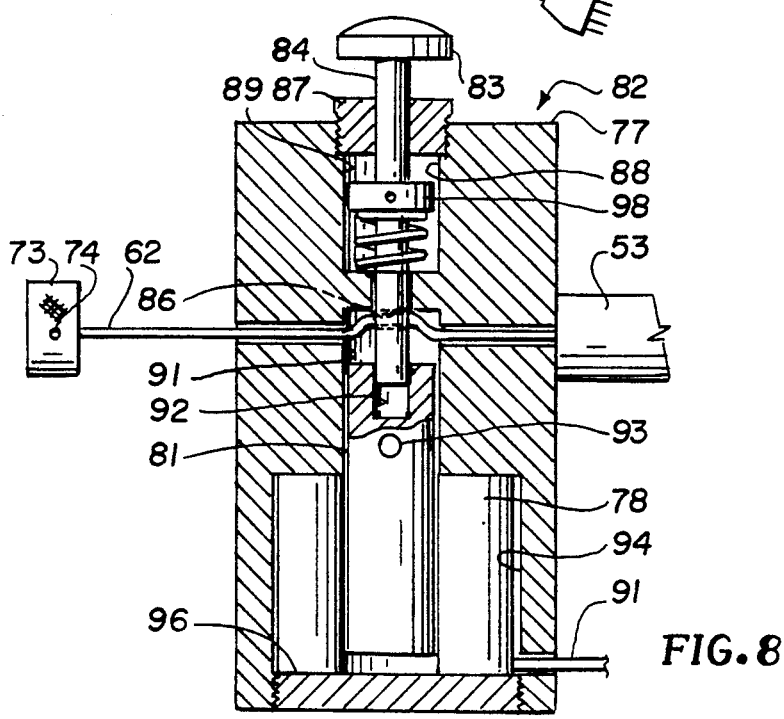
FIG. 8 is an enlarged detail view of the pressure sensing mechanism shown in FIG. 7.

In general, the endocardial catheter for mapping and/or ablation is for use in a chamber of the heart defined by a wall. The catheter is comprised of a flexible elongate tubular member having proximal and distal extremities. A push-pull element is provided having proximal and distal extremities and extends longitudinally of the elongate tubular member and has its distal extremity extending beyond the distal extremity of the tubular member. The push-pull element is movable axially in the tubular member. A plurality of circumferentially spaced apart flexible elongate arms having proximal and distal extremities are provided. Means is provided for securing the distal extremities of the arms to the distal extremity of the push-pull element. Means is also provided for securing the proximal extremities of the arms to the distal extremity of the tubular member whereby when the push-pull element is pulled proximally of the tubular member, the arms are caused to expand and bow outwardly to engage the wall of the chamber of the heart, and whereby when the push-pull element is pushed distally of the tubular member, the arms are caused to contract to move out of engagement with the wall of the heart. Means is carried by the tubular member and disposed between the tubular member and the arms for providing selective reinforcement of the arms and for urging said arms outwardly and into engagement with the wall of the heart to aid in yieldably retaining the arms and the electrodes in engagement with the wall of the heart.

More specifically as shown in the drawings, the endocardial catheter 11 for mapping and/or ablation with an expandable basket structure having means for selectively providing reinforcement to the basket structure with the exception of the means for selectively providing reinforcement is disclosed in co-pending application Ser. No. 07/656,764 filed Feb. 15, 1991. As described therein, it is for use in the chamber of a heart defined by a wall for performing mapping and/or ablation operations with respect to the wall of the heart. The catheter consists of a flexible elongate member 12 which is provided with proximal and distal extremities 13 and 14. A basket-like structure 16 is provided on the distal extremity 14 and consists of a plurality of longitudinally extending, circumferentially spaced apart arms 17 which are movable between a contracted position as shown in dotted lines in FIG. 1, and an expanded position such as that shown in solid lines in FIG. 1. The arms 17 are provided with proximal and distal extremities 18 and 19. The proximal extremities 18 are secured to the distal extremity 14 of the flexible elongate member 12 in a manner described in said co-pending application Ser. No. 07/656,764 filed Feb. 15, 1991. The distal extremities are fastened together in a cylindrical tip 21 provided with a hemispherical end. A plurality of longitudinally spaced apart electrodes 23 are provided on each of the arms 17 and are connected as disclosed in co-pending application Ser. No. 07/656,764 filed Feb. 15, 1991, to a plurality of conductors 24 extending through a lumen 26 provided in the flexible elongate member 12. The conductors 24 are connected to a cable 27 which is connected to a connector 28 that is adapted to be connected to a control console and power supply of the type described in co-pending application Ser. No. 07/656,764 filed Feb. 15, 1991.

Means is provided for moving the arms 17 between contracted and expanded positions, and consists of a push-pull wire 31 which is slidably and axially mounted in a lumen 32 provided in the flexible elongate member 12. As shown in FIG. 1, it extends distally to the distal extremity of the flexible elongate member 12 and is mounted in a fixture 33 by suitable means such as soldering. The fixture 33 is secured in the tip 21 by a suitable means such as an adhesive. The push-pull wire is provided with a knob 34 for operating the push-pull wire 31. By utilizing the knob 34 to push or pull on the push-pull wire 31 it can be seen that the flexible arm 17 can be moved between the dotted line and solid line positions shown in FIG. 1 for accomplishing mapping and/or ablation as hereinafter described.

The endocardial catheter thus far described is essentially the same as that disclosed in said co-pending application Ser. No. 07/656,764 filed Feb. 15, 1991. In order to provide selective reinforcement to the arms to ensure that the arms will remain in engagement with the wall of the heart when the arms have been moved to an expanded position, means is provided consisting of a secondary basket-like structure 36. The basket-like structure 36 consists of a plurality of longitudinally extending, circumferentially spaced apart arms 37 having proximal and distal extremities 38 and 39. The arms 37 serve as struts which are in circumferential alignment with the arms 17 of the basket-like structure 16. As can be seen in FIG. 1, the secondary basket-like structure 36 is disposed within the basket-like structure 16 and has a length which is slightly less than that of the basket-like structure 16. Thus, the proximal extremities of the arms 37 are secured to the distal extremity 14 of the flexible elongate member 12 distal of the region in which the proximal extremities 18 of the arms 17 are secured, as shown in FIG. 1. They are also secured in a manner similar to the manner of the proximal extremities 18 of the arms 17. The distal extremities 39 are secured to the distal extremities 19 of the arms 17 and are mounted in the tip 21.

In accordance with the present invention, it should be appreciated that additional basket-like structures can be provided to provide additional reinforcing as hereinafter described. For example, as shown in FIG. 1, a tertiary basket-like structure 41 is provided which consists of a plurality of longitudinally extending, circumferentially spaced apart arms 42 which are provided with proximal and distal extremities 43 and 44. As can be seen from FIG. 1, the length of the arms 42 is less than the length of the arms 37. The proximal extremities 43 are secured to the distal extremity 14 of the flexible elongate member 12 distally of the proximal extremities 38 and 18 of the arms 37 and 17, respectively. The distal extremities 44 are secured to the distal extremities 19 and 39, and are disposed within the tip 21.

The basket-like structures 16, 36 and 41 can be formed in a manner similar to that described in co-pending application Ser. No. 07/656,764 filed Feb. 15, 1991. Thus, sheets 51, 52 and 53 can be provided for the basket-like structures, with the sheet 51 being for the tertiary basket-like structure 41, sheet 52 for the secondary basket-like structure 36, and sheet 53 for the first-named, primary or outer basket-like structure 16. The sheets 51, 52 and 53 can be formed of a suitable flexible material such as plastic. One plastic found to be particularly suitable is polyimide. The sheet 51 has been provided with a plurality of longitudinally extending slits spaced transversely of the sheet 51. Similarly, sheet 52 is provided with a plurality of longitudinally extending slits 56 also spaced apart transversely of the sheet 52. Sheet 53 is similarly provided with a plurality of longitudinally extending, transversely spaced apart slits 57. Longitudinally spaced apart electrodes 23 are provided on the arms 17.

The basket-like structures 16, 36 and 41 are then formed by rolling the sheets 51, 52 and 53 onto mandrels and then bonding the proximal and distal extremities in the manner hereinbefore described to the distal extremity 14 of the flexible elongate member 12. The sheets 51, 52 and 53 are positioned so that the arms formed thereby are in registration or in alignment with each other.

Although the basket-like structures hereinbefore described have all been described as utilizing the polyimide material, it should be appreciated that particularly for the secondary and tertiary basket-like structures 36 and 37, if additional rigidity is required that this can be accomplished by utilizing plastic-coated stainless steel sheets to provide such additional rigidity rather than utilizing plastic by itself.

In utilizing the endocardial catheter which is shown in FIG. 1, the pull wire can be pulled rearwardly to cause expansion of the basket-like structures 16, 36 and 41 in the manner shown in FIG. 1. The secondary basket-like structure 36 provides reinforcement to the portions of the basket-like structure 16 extending distally from the midpoint of the same to help ensure that those portions of the basket-like structure 16 and the electrodes 23 carried thereby will remain in contact with the wall of the heart as the heart wall moves while it is beating. Similarly, the tertiary basket-like structure 41 provides reinforcement to the arms of the secondary basket-like structure 36, and therethrough to the arms of the primary basket-like structure 16 to further ensure that the arms 17 will remain in engagement with the wall of the heart during the time that the heart is beating and during which measurement and/or ablation operations are accomplished, of the type described in co-pending application Ser. No. 07/656,764 filed Feb. 15, 1991.

It should be appreciated that although secondary and tertiary basket-like structures 36 and 41 have been provided, it is desirable that the distal extremity of the catheter 11 still remain relatively flexible so that it can be readily introduced into the various chambers of the heart. For that reason, a relatively flexible material is desired for use in making the arms of the basket-like structures. In addition, the basket-like structures should have a relatively minimum profile when the basket-like structures 16, 36 and 41 are in their contracted positions.

Another embodiment of the invention is shown in FIG. 7, in which a pressure sensing mechanism is shown which will give an indication of the force applied to the push-pull wire 31 after the basket assemblies 16, 36 and 41 have been moved to expanded positions. Such an endocardial catheter for mapping and/or ablation 51 is shown in FIG. 7. The catheter consists of a flexible elongate member 52 provided with proximal and distal extremities 53 and 54. A basket assembly 56 of the same general type as hereinbefore described is provided on the distal extremity 54 of the flexible elongate member 52. The basket assembly 56 consists of a primary or outer basket assembly 57 which is similar to the basket-like structure 16 provided in the previous embodiment and a secondary basket assembly 58 which is similar to the secondary basket-like structure 36 provided in the previous embodiment. In this embodiment of the invention, only two of such basket assemblies are provided, rather than three as in the previous embodiment. A rounded tip 61 is provided for the basket assemblies which has mounted therein a push-pull wire 62 which extends axially through the flexible elongate member 52. The primary basket assembly 57 is provided with electrodes 66 of the type hereinbefore described which are connected to conductors (not shown) which underlie the electrodes and which are connected to conductors (not shown) extending through the flexible elongate member 52 that are connected to a cable 67. The cable 67 is connected to a connector 68 and a control console and power supply of the type described in copending application Ser. No. 07/656,764 filed Feb. 15, 1991. A push-pull wire 62 is provided with proximal and distal extremities 71 and 72 in which the distal extremity 72 is connected to the tip 61. A knurled knob 73 is secured to the proximal extremity 71 by a set screw 74.

A pressure transducer assembly 76 is mounted on the proximal extremity 53 of the flexible elongate member 52. The pressure transducer assembly consists of a housing 77. A strain gauge 78 of a conventional type is mounted within the housing and is provided with a lever arm 81 which is secured to a releasable attachment mechanism 82 which is provided with a pushbutton 83. The pushbutton 83 has a rigid stem 84 having a hole 86 through which the push-pull wire 62 extends. The stem 84 extends through a cap 87 threaded into the housing 77 above a well 88 in the housing 77. The stem 84 also extends through a bore 89 in the housing 77 and through another bore 91 in the housing 77 into which one extremity of the lever arm 81 extends. The stem 84 extends into and is movable axially into a bore 92 provided in the lever arm 81. The lever arm 81 is pivotally mounted on a pin 93 which serves as a fulcrum. The strain gauge 78 is disposed in a bore 94 in the housing 77 and is retained therein by a threaded cap 96.

The push-pull wire 62 extends through a bore 97 in the housing 77. Means is provided for yieldably urging the stem 84 having the push-pull wire 62 extending therethrough in a direction substantially perpendicular to the longitudinal axis of the pull wire and consists of a coil spring 98 seated in the well 88 and having one end engaging a collar 98 mounted on the stem 84 and secured thereto by a set screw 99. Thus, it can be seen that the pushbutton 83 is movable between a normally clamping position securing the push-pull wire 62 to the lever arm 81 to a released position in which the push-pull wire 62 can be moved relative to the stem 84 to permit expansion and contraction of the primary basket assembly 57.

When the pushbutton 83 is depressed, it releases the push-pull wire 62 and permits movement of the same under the control of the knob 73. After the push-pull wire 62 has been pulled proximally a sufficient distance to expand the basket assembly 57 into the desired position in the chamber of the heart so that it is believed that the electrodes 66 carried thereby are engaged with the wall of the heart, the pushbutton 83 is released to frictionally engage the pull wire so that the forces which are encountered by the arms of the basket assembly are transmitted through the push-pull wire 62 to the strain gauge transducer 78 which supplies an electrical output through a cable 101. The cable 91 is connected to an instrument 102 which is provided with a gauge 103. The gauge 103 includes a movable needle 104 to give an indication of the force which is being encountered by the push-pull wire 62 as indicated on a scale 106 which, for example, can be calibrated in dynes.

By watching the movement of the needle 104 and thereby the force which is being applied to the push-pull wire 62, it can be seen whether or not there is a change in pressure with the beating of the heart. If there is substantially no change in pressure, this indicates that the basket assembly 56 has not been expanded sufficiently because the arms of the basket assembly 56 are not in engagement with the wall of the heart. When the arms of the basket assembly 56 are in engagement with the wall of the heart, the beating of the heart will cause the movement of the basket assembly 56 and thereby increase the force being applied to the push-pull wire 62 which will be recorded on the instrument 102. The additional force on the push-pull wire 62 will cause additional force to be applied to the lever arm 81, which force will be measured by the strain gauge 78. If the pressure movement being sensed by the transducer assembly 96 is following the beating of the heart, this indicates that the basket assembly 56 is continuously in engagement with the endocardium or wall of the heart. As soon as this is the case, the mapping measurements desired can be made.

This pressure transducer assembly or mechanism makes it possible to overcome the difficulty which may be present during fluoroscopy in which it is possible to see the basket assembly 56 but it is not possible to see the walls of the heart since they are transparent to x-rays, making it difficult to ascertain whether or not the basket assembly has been expanded sufficiently to engage the wall of the heart during all positions of the wall of the heart during beating of the heart. Thus it can be seen that the pressure gauge of the present invention makes it possible to ascertain pressures applied by the beating heart as it squeezes and releases the basket assembly 56 which causes the changes in pressure to be transferred as a force through the push-pull wire 62.

From the foregoing it can be seen that there has been provided an endocardial catheter for mapping and/or ablation with an expandable basket structure having means for providing selective reinforcement and a pressure sensing mechanism for use therewith. The reinforcement is provided to ensure that the electrodes carried by the basket assembly are maintained in engagement with the endocardium of the heart during beating of the heart. Supplemental basket structures are provided to ensure that all portions of the basket structure engage the endocardium of the heart. The pressure sensing means makes it possible to ascertain whether or not the electrodes are continuously in engagement with the endocardium of the heart during beating of the heart.

What is claimed is:

1. An endocardial catheter for mapping and/or ablation for use in a chamber of the heart defined by a wall, comprising a flexible elongate tubular member having proximal and distal extremities, a primary basket assembly secured to the distal extremity of the flexible elongate member, said primary basket assembly having a plurality of longitudinally extending, circumferentially spaced apart arms having proximal and distal extremities and having outer surfaces, a plurality of electrodes mounted on said arms of said primary basket assembly and facing in directions outwardly away from said outer surfaces, a secondary basket assembly having a plurality of longitudinally extending, circumferentially spaced apart arms with the arms being generally in alignment with the arms of the primary basket assembly, a push-pull wire extending through the flexible elongate member and having proximal and distal extremities, means securing the distal extremity of the push-pull wire to the distal extremities of the arms of the primary and secondary basket assemblies, means bonding the proximal extremities of the primary and secondary basket assemblies to the distal extremity of the flexible elongate tubular member, and means secured to the proximal extremity of the push-pull wire for moving the push-pull wire to cause the primary and secondary basket assemblies to be moved between expanded and contracted positions in which the arms of the secondary basket assembly are moved into engagement with at least portions of the arms of the primary basket assembly for providing selective reinforcement of the arms of the primary basket assembly and for yieldably urging the arms of the primary basket assembly outwardly and into engagement with the wall of the heart to yieldably retain the arms of the primary basket assembly and the electrodes carried thereby in engagement with the wall of the heart and conductive means carried by the flexible elongate member and coupled to said electrodes.

2. A catheter as in claim 1 together with a tertiary basket assembly disposed within the secondary basket assembly and having longitudinally extending arms which are circumferentially spaced apart and are in circumferential alignment with the arms of the secondary basket assembly, said arms of the tertiary basket assembly having proximal and distal extremities, means securing the proximal extremities of the tertiary basket assembly to the distal extremity of the flexible elongate element and means for securing the distal extremities of the tertiary basket assembly to the distal extremities of the first and second basket assemblies.

3. A catheter as in claim 1 wherein said arms of said primary and secondary basket assemblies are comprised of a plastic material.

4. A catheter as in claim 1 together with force measuring means engaging the push-pull wire for measuring the force applied to the push-pull wire by the basket assemblies during beating of the heart.

5. A catheter as in claim 4 wherein said force measuring means includes strain gauge measuring means and releasable means releasably securing said strain gauge measuring means to said push-pull wire.

6. A catheter as in claim 5 wherein said releasable means releasably securing said strain gauge measuring means to said push-pull wire includes means for normally clamping said push-pull wire and being movable between released and clamping positions whereby in the released position the push-pull wire can be moved to permit expansion and contraction of the primary basket assembly.

7. An endocardial catheter for mapping and/or ablation for use in a chamber of a heart defined by a wall, comprising a flexible elongate tubular member having proximal and distal extremities, a basket assembly mounted on the distal extremity of the flexible elongate member, said basket assembly being comprised of a plurality of longitudinally extending, circumferentially spaced apart arms having proximal and distal extremities, means securing the proximal extremities of the arms to the distal extremity of the flexible elongate tubular member, a push-pull element having proximal and distal extremities extending longitudinally of the tubular member and beyond the distal extremity of the tubular member and movable axially of the tubular member, means securing the distal extremities of the arms to the distal extremity of the push-pull element whereby upon axial movement of the push-pull element, the basket assembly can be moved between expanded and contracted positions, and means carried by the distal extremity of the flexible elongate tubular member and being disposed within the basket assembly and having portions movable into engagement with portions of the arms for providing selective reinforcement of the arms and for yieldably urging said arms outwardly and into engagement with the wall of the heart to aid in yieldably retaining the arms in engagement with the wall of the heart.

8. A catheter as in claim 7 wherein said means disposed within the basket includes an additional basket assembly comprised of a plurality of longitudinally extending, circumferentially spaced apart arms having proximal and distal extremities, means securing the proximal extremities of the arms of the additional basket assembly to the distal extremity of the flexible elongate element, means for securing the distal extremities of the arms of the additional basket assembly to the push-pull wire so that as the pull wire is retracted and moved in a proximal direction, the additional basket assembly is moved into engagement with the first named basket assembly and the first named basket assembly is moved into engagement with the wall of the heart.

9. A catheter as in claim 7 together with means for sensing the force applied to the push-pull element by the basket assembly as the heart is beating to ascertain whether the arms of the basket assembly remain in engagement with the wall of the heart during beating of the heart.

10. An endocardial catheter for mapping and/or ablation for use in a chamber of a heart defined by a wall, comprising a flexible elongate tubular member having proximal and distal extremities, a basket assembly mounted on the distal extremity of the flexible elongate member, said basket assembly being movable between expanded and contracted positions, said basket assembly having electrodes carried thereby adapted to be moved into engagement with the wall of the heart, a push-pull element having proximal and distal extremities extending longitudinally of the tubular member and extending beyond the distal extremity of the tubular member and movable axially of the tubular member, said basket assembly having proximal and distal extremities, means securing the proximal extremity of the basket assembly to the distal extremity of the tubular member, means securing the distal extremity of the basket assembly to the distal extremity of the push-pull element and means secured to the proximal extremity of the flexible elongate member and secured to the push-pull element for sensing the force being applied to the push-pull element by the basket assembly as the heart is beating to ascertain whether or not the electrodes carried by the basket assembly are in continuous engagement with the wall of the heart during beating of the heart.

11. A catheter as in claim 10 wherein said means for sensing the force includes means for engaging the push-pull element and being movable between a clamping position and a released position whereby in the released position movement of the push-pull wire is permitted for causing expansion and contraction of the basket assembly.

12. In a method for performing mapping and ablation in a chamber of a heart defined by a wall, utilizing a catheter comprised of a flexible elongate tubular element having proximal and distal extremities and a basket assembly having electrodes carried thereby and having an inner surface and being movable between contracted and expanded positions mounted on the distal extremity of the flexible elongate element, introducing the catheter into the body so that the basket assembly is disposed in a chamber of the heart, moving the basket assembly to an expanded position and yieldably applying forces by use of a structural member to engage the interior surface of the basket assembly so that the electrodes carried by the basket assembly are maintained in engagement with the wall of the heart during beating of the heart.

13. A method for performing mapping and ablation in a chamber of a heart defined by a wall, comprising utilizing a catheter comprised of a flexible elongate tubular element having proximal and distal extremities and a basket assembly having electrodes carried thereby and being movable between contracted and expanded positions mounted on the distal extremity of the flexible elongate element, introducing the catheter into the body so that the basket assembly is disposed in a chamber of the heart, moving the basket assembly to an expanded position and yieldably reinforcing the basket assembly so that the electrodes carried by the basket assembly are maintained in engagement with the wall of the heart during beating of the heart and sensing the force applied to the basket assembly by the wall of the heart to ascertain whether the basket assembly is continuously in engagement with the wall of the heart during beating of the heart.

* * * * *